(12) United States Patent
Powlesland et al.

(10) Patent No.: US 10,851,366 B2
(45) Date of Patent: Dec. 1, 2020

(54) PEPTIDES DERIVED FROM LENGSIN (LGSN), COMPLEXES COMPRISING SUCH PEPTIDES BOUND TO MHC MOLECULES

(71) Applicants: IMMUNOCORE LIMITED, Oxfordshire (GB); ADAPTIMMUNE LIMITED, Oxfordshire (GB)

(72) Inventors: Alex Powlesland, Abingdon (GB); Maurits Kleijnen, Abingdon (GB)

(73) Assignee: IMMUNOCORE LIMITED, Oxfordshire (GB)

( * ) Notice: Subject to any disclaimer, the term of this patent is extended or adjusted under 35 U.S.C. 154(b) by 165 days.

(21) Appl. No.: 15/777,621

(22) PCT Filed: Nov. 23, 2016

(86) PCT No.: PCT/GB2016/053659
§ 371 (c)(1),
(2) Date: May 18, 2018

(87) PCT Pub. No.: WO2017/089777
PCT Pub. Date: Jun. 1, 2017

(65) Prior Publication Data
US 2018/0327736 A1    Nov. 15, 2018

(30) Foreign Application Priority Data
Nov. 23, 2015 (GB) .................................. 1520589.1

(51) Int. Cl.
*C07K 16/40* (2006.01)
*C12N 9/00* (2006.01)
*C07K 14/47* (2006.01)
*G01N 33/573* (2006.01)
*A61K 38/00* (2006.01)

(52) U.S. Cl.
CPC ............ *C12N 9/93* (2013.01); *C07K 14/4748* (2013.01); *C07K 16/40* (2013.01); *G01N 33/573* (2013.01); *A61K 38/00* (2013.01); *G01N 2333/9015* (2013.01)

(58) Field of Classification Search
CPC ....... C12N 9/93; C07K 14/4748; C07K 16/40
USPC ...................................................... 424/139.1
See application file for complete search history.

(56) References Cited

U.S. PATENT DOCUMENTS

2010/0015101 A1* 1/2010 Sato .................... A61K 39/0011
424/93.7

* cited by examiner

*Primary Examiner* — Yan Xiao
(74) *Attorney, Agent, or Firm* — Fenwick & West LLP; Andrea Nichols (57) ABSTRACT

The present invention relates to novel peptides derived from Lengsin (LGSN), complexes comprising such peptides bound to recombinant MHC molecules, and cells presenting said peptide in complex with MHC molecules. Also provided by the present invention are binding moieties that bind to the peptides and/or complexes of the invention. Such moieties are useful for the development of immunotherapeutic reagents for the treatment of diseases such as cancer.

10 Claims, 5 Drawing Sheets
Specification includes a Sequence Listing.

LGSN - ALGETFIRYFV

TCR1

Alpha chain variable region

K Q E V T Q I P A A L S V P E G E N L V L N C S F T D S A I Y N L Q W F R Q
D P G K G L T S L L L I Q S S Q R E Q T S G R L N A S L D K S S G R S T L Y
I A A S Q P G D S A T Y L C A V M D S S Y K L I F G S G T R L L V R P

Beta chain variable region

N A G V T Q T P K F Q V L K T G Q S M T L Q C A Q D M N H N S M Y W Y R Q D
P G M G L R L I Y Y S A S E G T T D K G E V P N G Y N V S R L N K R E F S L
R L E S A A P S Q T S V Y F C A S G F Y G Y T F G S G T R L T V V

TCR2

Alpha chain variable region

K Q E V T Q I P A A L S V P E G E N L V L N C S F T D S A I Y N L Q W F R Q
D P G K G L T S L L L I Q S S Q R E Q T S G R L N A S L D K S S G R S T L Y
I A A S Q P G D S A T Y L C A V R G Y Q K V T F G T G T K L Q V I P

Beta chain variable region

N A G V T Q T P K F Q V L K T G Q S M T L Q C A Q D M N H E Y M S W Y R Q D
P G M G L R L I H Y S V G A G I T D Q G E V P N G Y N V S R S T T E D F P L
R L L S A A P S Q T S V Y F C A S S P G I G E L F F G E G S R L T V L

TCR3

Alpha chain variable region

K Q E V T Q I P A A L S V P E G E N L V L N C S F T D S A I Y N L Q W F R Q
D P G K G L T S L L L I Q S S Q R E Q T S G R L N A S L D K S S G R S T L Y
I A A S Q P G D S A T Y L C A V R A Q G S E K L V F G K G T K L T V N P

Beta chain variable region

N A G V T Q T P K F R I L K I G Q S M T L Q C T Q D M N H N Y M Y W Y R Q D
P G M G L K L I Y Y S V G A G I T D K G E V P N G Y N V S R S T T E D F P L
R L E L A A P S Q T S V Y F C A S S Y L G Q D P E G A E A F F G Q G T R L T
V V

PEPTIDES DERIVED FROM LENGSIN (LGSN), COMPLEXES COMPRISING SUCH PEPTIDES BOUND TO MHC MOLECULES

CROSS-REFERENCE TO RELATED APPLICATIONS

This application is the National Stage of International Application No. PCT/GB2016/053659, filed Nov. 23, 2016, which claims the benefit of and priority to Great Britain Patent Application Serial No. 1520589.1, filed on Nov. 23, 2015, the contents of which are incorporated by reference in their entirety.

The present invention relates to novel peptides derived from Lengsin (LGSN), complexes comprising such peptides bound to recombinant MHC molecules, and cells presenting said peptide in complex with MHC molecules. Also provided by the present invention are binding moieties that bind to the peptides and/or complexes of the invention. Such moieties are useful for the development of immunotherapeutic reagents for the treatment of diseases such as cancer.

T cells are a key part of the cellular arm of the immune system. They specifically recognise peptide fragments that are derived from intracellular proteins and presented in complex with Major Histocompatibility Complex (MHC) molecules on the surface of antigen presenting cells (APCs). In humans, MHC molecules are known as human leukocyte antigens (HLA), and both terms are used synonymously herein. MHC molecules have a binding groove in which the peptide fragments bind. Recognition of particular peptide-MHC antigens is mediated by a corresponding T cell receptor (TCR). Tumour cells express various tumour associated antigens (TAA) and peptides derived from these antigens may be displayed on the tumour cell surface. Detection of a MHC class I-presented TAA-derived peptide by a CD8+ T cell bearing the corresponding T cell receptor, leads to targeted killing of the tumour cell. However, as a consequence of the selection processes which occur during T cell maturation in the thymus, there is a scarcity of T cells (and TCRs) in the circulating repertoire, which recognise TAA-derived peptides with a sufficiently high level of affinity. Therefore tumour cells often escape detection.

The identification of particular TAA-derived peptides presented by MHC molecules on tumour cells enables the development of novel immunotherapeutic reagents designed to specifically target and destroy said tumour cells. Such reagents may be moieties that bind to the TAA-derived peptide and/or complexes of peptide and MHC and they typically function by inducing a T cell response. For example, such reagents may be based, exclusively, or in part, on T cells, or T cell receptors (TCRs), or antibodies. The identification of suitable TAAs for therapeutic targeting requires careful consideration in order to mitigate off-tumour on-target toxicity in a clinical setting. TAAs that are suitable as targets for immunotherapeutic intervention should show a sufficient difference in expression levels between tumour tissue and normal, healthy tissues; in other words there should be a suitable therapeutic window, which will enable targeting of tumour tissue and minimise targeting healthy tissues. Ideally TAAs are highly expressed in tumour tissue and have limited or no expression in normal healthy tissue. Typically, a person skilled in the art would use protein expression data to identify whether a therapeutic window exists for a given TAA. Higher protein expression being indicative of higher levels of peptide-MHC presented peptide on the cell surface. The inventors of the present application have found that differences in RNA expression, rather than protein expression is a more reliable indicator of pMHC levels and consequently the therapeutic window.

It is therefore desirable to provide peptides derived from TAAs with a suitable therapeutic window, based on RNA expression, MHC complexes thereof and binding moieties that can be used for the development of new cancer therapies. Furthermore, it is desirable that said peptides are not identical to, or highly similar to, any other MHC restricted peptide, derived from an alternative protein(s), and presented by MHC on the surface of non-cancerous cells. The existence of such peptide mimics increase the risk of in vivo toxicity for targeted cancer therapies.

In silico algorithms, such as SYFPETHEI (Rammensee, et al., Immunogenetics. 1999 November; 50(3-4):213-9 (access via svfpeithi.de) and BIMAS (Parker, et al., J. Immunol. 1994 Jan. 1; 152(1):163-75 (access via www-birnas.cit.nih.gov/molbio/hla_bind/)) are available to predict the amino acid sequences of MHC-presented peptides derived from proteins. However, these methods are known to generate a high proportion of false positives (since they simply define the likelihood of a given peptide being able to bind a given MHC and do not account for intracellular processing). Therefore, it is not possible to accurately predict whether a given peptide-MHC is actually presented by tumour cells. Direct experimental data is typically required.

LGSN (also known as lengsin or glutamate-ammonia ligase domain-containing protein 1 or lens glutamine synthase-like and having Uniprot accession number Q5TDP6) is a ligase involved in terminal differentiation in the lens. LGSN has been associated with cancer (Nakatsugawa et al. Cancer Sci. 2009 August; 100(8):1485-93). LGSN is an ideal target for immunotherapeutic applications. The inventors have found that LGSN has a particularly suitable therapeutic window based on RNA expression. The inventors have found novel peptides derived from LGSN that are presented on the cell surface in complex with MHC. These peptides are particularly useful for the development of reagents that can targets cells expressing LGSN and for the treatment of cancers, including non small cell lung cancer (adenocarcinoma).

In a first aspect, the invention provides a peptide comprising, consisting essentially of, or consisting of
(a) the amino acid sequence of any one of SEQ ID NOS: 1-3, or
(b) the amino acid sequence of any one of SEQ ID NOs: 1-3 with the exception of 1, 2 or 3 amino acid substitutions, and/or 1, 2 or 3 amino acid insertions, and/or 1, 2 or 3 amino acid deletions,
wherein the peptide forms a complex with a Major Histocompatibility Complex (MHC) molecule.

The inventors have found that peptides of the invention are presented by MHC on the surface of tumour cells. Accordingly, the peptides of the invention, as well as moieties that bind the peptide-MHC complexes, can be used to develop therapeutic reagents.

| SEQ ID NO | Amino acid sequence |
|---|---|
| 1 | ALGETFIRYFV |
| 2 | LSCLMAPSV |
| 3 | QILTPPQL |

In a preferred embodiment the peptides have the following sequences:

1    ALGETFIRYFV

As is known in the art the ability of a peptide to form an immunogenic complex with a given MHC type, and thus activate T cells, is determined by the stability and affinity of the peptide-MHC interaction (van der Burg et al. J Immunol. 1996 May 1; 156(9):3308-14). The skilled person can, for example, determine whether or not a given polypeptide forms a complex with an MHC molecule by determining whether the MHC can be refolded in the presence of the polypeptide using the process set out in Example 2. If the polypeptide does not form a complex with MHC then MHC will not refold. Refolding is commonly confirmed using an antibody that recognises MHC in a folded state only. Further details can be found in Garboczi et al., Proc Natl Acad Sci USA. 1992 Apr. 15; 89(8):3429-33. Alternatively, the skilled person may determine the ability of a peptide to stabilise MHC on the surface of TAP-deficient cell lines such as T2 cells, or other biophysical methods to determine interaction parameters (Harndahl et al. J Biomol Screen. 2009 February; 14(2):173-80).

Preferably, peptides of the invention are from about 8 to about 16 amino acids in length, and are most preferably 8, 9, or 10 or 11 amino acids in length, most preferably 11 amino acids in length.

The peptides of the invention may consist or consist essentially of the amino acids sequences provided in SEQ ID NOs: 1-3.

The amino acid residues comprising the peptides of the invention may be chemically modified. Examples of chemical modifications include those corresponding to post translational modifications for example phosphorylation, acetylation and deamidation (Engelhard et al., Curr Opin Immunol. 2006 February; 18(1):92-7). Chemical modifications may not correspond to those that may be present in vivo. For example, the N or C terminal ends of the peptide may be modified improve the stability, bioavailability and or affinity of the peptides (see for example, Brinckerhoff et al *Int J Cancer*, 1999 Oct. 29; 83(3):326-34). Further examples of non-natural modifications include incorporation of non-encoded α-amino acids, photoreactive cross-linking amino acids, N-methylated amino acids, and β-amino acids, backbone reduction, retroinversion by using d-amino acids, N-terminal methylation and C-terminal amidation and pegylation.

Amino acid substitution means that an amino acid residue is substituted for a replacement amino acid residue at the same position. Inserted amino acid residues may be inserted at any position and may be inserted such that some or all of the inserted amino acid residues are immediately adjacent one another or may be inserted such that none of the inserted amino acid residues is immediately adjacent another inserted amino acid residue. One, two or three amino acids may be deleted from the sequence of SEQ ID NOs: 1-3. Each deletion can take place at any position of SEQ ID NOs: 1-3.

In some embodiments, the polypeptide of the invention may comprise one, two or three additional amino acids at the C-terminal end and/or at the N-terminal end of the sequence of SEQ ID NOs: 1-3. A polypeptide of the invention may comprise the amino acid sequence of SEQ ID NOs: 1-3 with the exception of one amino acid substitution and one amino acid insertion, one amino acid substitution and one amino acid deletion, or one amino acid insertion and one amino acid deletion. A polypeptide of the invention may comprise the amino acid sequence of SEQ ID NOs: 1-3, with the exception of one amino acid substitution, one amino acid insertion and one amino acid deletion.

Inserted amino acids and replacement amino acids may be naturally occurring amino acids or may be non-naturally occurring amino acids and, for example, may contain a non-natural side chain, and/or be linked together via non-native peptide bonds. Such altered peptide ligands are discussed further in Douat-Casassus et al., J. Med. Chem, 2007 Apr. 5; 50(7):1598-609 and Hoppes et al., J. Immunol 2014 Nov. 15; 193(10):4803-13 and references therein). If more than one amino acid residue is substituted and/or inserted, the replacement/inserted amino acid residues may be the same as each other or different from one another. Each replacement amino acid may have a different side chain to the amino acid being replaced.

Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 asp, asn, glu, gln; Group 3 His, Arg, Lys; Group 4 Met, Leu, Ile, Val, Cys; Group 5 Phe Thy Trp.

Preferably, polypeptides of the invention bind to MHC in the peptide binding groove of the MHC molecule. Generally the amino acid modifications described above will not impair the ability of the peptide to bind MHC. In a preferred embodiment, the amino acid modifications improve the ability of the peptide to bind MHC. For example, mutations may be made at positions which anchor the peptide to MHC. Such anchor positions and the preferred residues at these locations are known in the art, particularly for peptides which bind HLA-A*02 (see, e.g. Parkhurst et al., *J. Immunol.* 1996 Sep. 15; 157(6):2539-48 and Parker et al. J Immunol. 1992 Dec. 1; 149(11):3580-7). Amino acids residues at position 2, and at the C terminal end, of the peptide are considered primary anchor positions. Preferred anchor residues may be different for each HLA type. The preferred amino acids in position 2 for HLA-A*02 are Leu, Ile, Val or Met. At the C terminal end, a valine or leucine is favoured.

A peptide of the invention may be used to elicit an immune response. If this is the case, it is important that the immune response is specific to the intended target in order to avoid the risk of unwanted side effects that may be associated with an "off target" immune response. Therefore, it is preferred that the amino acid sequence of a peptide of the invention does not match the amino acid sequence of a peptide from any other protein(s), in particular, that of another human protein. A person of skill in the art would understand how to search a database of known protein sequences to ascertain whether a peptide according to the invention is present in another protein.

Peptides of the invention may be conjugated to additional moieties such as carrier molecules or adjuvants for use as vaccines (for specific examples see Liu et al. Bioconjug Chem. 2015 May 20; 26(5): 791-801 and references therein). The peptides may be biotinylated or include a tag, such as a His tag. Examples of adjuvants used in cancer vaccines include microbes, such as the bacterium *Bacillus* Calmette-Guérin (BCG), and/or substances produced by bacteria, such as Detox B (an oil droplet emulsion of monophosphoryl lipid A and mycobacterial cell wall skeleton). KLH (keyhole limpet hemocyanin) and bovine serum albumin are examples of suitable carrier proteins used in vaccine compositions Alternatively or additionally, the peptide may attached, covalently or otherwise, to proteins such as MHC molecules and/or antibodies (for example, see King et al. *Cancer Immunol Immunother.* 2013 June; 62(6):1093-105). Alternatively or additionally the peptides may be encapsulated into liposomes (for example see Adamina et al *Br J Cancer.* 2004 Jan. 12; 90(1):263-9). Such modified peptides may not correspond to any molecule that exists in nature.

Peptides of the invention can be synthesised easily by Merrifield synthesis, also known as solid phase synthesis, or any other peptide synthesis methodology. GMP grade peptide is produced by solid-phase synthesis techniques by Multiple Peptide Systems, San Diego, Calif. As such, the peptides may be immobilised, for example to a solid support such as a bead. Alternatively, the peptide may be recombinantly produced, if so desired, in accordance with methods known in the art. Such methods typically involve the use of a vector comprising a nucleic acid sequence encoding the peptide to be expressed, to express the polypeptide in vivo; for example, in bacteria, yeast, insect or mammalian cells. Alternatively, in vitro cell-free systems may be used. Such systems are known in the art and are commercially available for example from Life Technologies, Paisley, UK. The peptides may be isolated and/or may be provided in substantially pure form. For example, they may be provided in a form which is substantially free of other peptides or proteins.

In a second aspect the invention provides a complex of the peptide of the first aspect and an MHC molecule. Preferably, the peptide is bound to the peptide binding groove of the MHC molecule. The MHC molecule may be MHC class I. The MHC class I molecule may be selected from HLA-A*02, HLA-A*01, HLA-A*03, HLA-A11, HLA-A23, HLA-A24, HLA-B*07, HLA-B*08, HLA-B40, HLA-B44, HLA-B15, HLA-C*04, HLA*C*03 HLA-C*07. As is known to those skilled in the art there are allelic variants of the above HLA types, all of which are encompassed by the present invention. A full list of HLA alleles can be found on the EMBL Immune Polymorphism Database (http://www.ebi.ac.uk/ipd/imgt/hla/allele.html; Robinson et al. Nucleic Acids Research (2015) 43:D423-431). The MHC molecule may be HLA-A*02.

The complex of the invention may be isolated and/or in a substantially pure form. For example, the complex may be provided in a form which is substantially free of other peptides or proteins. It should be noted that in the context of the present invention, the term "MHC molecule" includes recombinant MHC molecules, non-naturally occurring MHC molecules and functionally equivalent fragments of MHC, including derivatives or variants thereof, provided that peptide binding is retained. For example, MHC molecules may be fused to a therapeutic moiety, attached to a solid support, in soluble form, attached to a tag, biotinylated and/or in multimeric form. The peptide may be covalently attached to the MHC.

Methods to produce soluble recombinant MHC molecules with which peptides of the invention can form a complex are known in the art. Suitable methods include, but are not limited to, expression and purification from *E. coli* cells or insect cells. A suitable method is provided in Example 2 herein. Alternatively, MHC molecules may be produced synthetically, or using cell free systems.

Polypeptides and/or polypeptide-MHC complexes of the invention may be associated (covalently or otherwise) with a moiety capable of eliciting a therapeutic effect. Such a moiety may be a carrier protein which is known to be immunogenic. KLH (keyhole limpet hemocyanin) and bovine serum albumin are examples of suitable carrier proteins used in vaccine compositions. Alternatively, the peptides and/or peptide-MHC complexes of the invention may be associated with a fusion partner. Fusion partners may be used for detection purposes, or for attaching said peptide or MHC to a solid support, or for MHC oligomerisation. The MHC complexes may incorporate a biotinylation site to which biotin can be added, for example, using the BirA enzyme (O'Callaghan et al., 1999 Jan. 1; 266(1):9-15). Other suitable fusion partners include, but are not limited to, fluorescent, or luminescent labels, radiolabels, nucleic acid probes and contrast reagents, antibodies, or enzymes that produce a detectable product. Detection methods may include flow cytometry, microscopy, electrophoresis or scintillation counting. Fusion partners may include cytokines, such as interleukin 2, interferon alpha, and granulocyte-macrophage colony-stimulating factor.

Peptide-MHC complexes of the invention may be provided in soluble form, or may be immobilised by attachment to a suitable solid support. Examples of solid supports include, but are not limited to, a bead, a membrane, sepharose, a magnetic bead, a plate, a tube, a column. Peptide-MHC complexes may be attached to an ELISA plate, a magnetic bead, or a surface plasmon resonance biosensor chip. Methods of attaching peptide-MHC complexes to a solid support are known to the skilled person, and include, for example, using an affinity binding pair, e.g, biotin and streptavidin, or antibodies and antigens. In a preferred embodiment peptide-MHC complexes are labelled with biotin and attached to streptavidin-coated surfaces.

Peptide-MHC complexes of the invention may be in multimeric form, for example, dimeric, or tetrameric, or pentameric, or octomeric, or greater. Examples of suitable methods for the production of multimeric peptide MHC complexes are described in Greten et al., Clin. Diagn. Lab. Immunol. 2002 March; 9(2):216-20 and references therein. In general, peptide-MHC multimers may be produced using peptide-MHC tagged with a biotin residue and complexed through fluorescent labelled streptavidin. Alternatively, multimeric peptide-MHC complexes may be formed by using immunoglobulin as a molecular scaffold. In this system, the extracellular domains of MHC molecules are fused with the constant region of an immunoglobulin heavy chain separated by a short amino acid linker. Peptide-MHC multimers have also been produced using carrier molecules such as dextran (WO02072631). Multimeric peptide MHC complexes can be useful for improving the detection of binding moieties, such as T cell receptors, which bind said complex, because of avidity effects.

The polypeptides of the invention may be presented on the surface of a cell in complex with MHC. Thus, the invention also provides a cell presenting on its surface a complex of the invention. Such a cell may be a mammalian cell, preferably a cell of the immune system, and in particular a specialised antigen presenting cell such as a dendritic cell or a B cell. Other preferred cells include T2 cells (Hosken, et al., Science. 1990 Apr. 20; 248(4953):367-70). Cells presenting the polypeptide or complex of the invention may be isolated, preferably in the form of a population, or provided in a substantially pure form. Said cells may not naturally present the complex of the invention, or alternatively said cells may present the complex at a level higher than they would in nature. Such cells may be obtained by pulsing said cells with the polypeptide of the invention. Pulsing involves incubating the cells with the polypeptide for several hours using polypeptide concentrations typically ranging from $10^{-5}$ to $10^{-12}$ M. Said cells may additionally be transduced with HLA molecules, such as HLA-A*02 to further induce presentation of the peptide. Cells may be produced recombinantly. Cells presenting peptides of the invention may be used to isolate T cells and T cell receptors (TCRs) which are activated by, or bind to, said cells, as described in more detail below.

In a third aspect, the invention provides a nucleic acid molecule comprising a nucleic acid sequence encoding the polypeptide of the first aspect of the invention. The nucleic acid may be cDNA. The nucleic acid molecule may consist essentially of a nucleic acid sequence encoding the peptide of the first aspect of the invention or may encode only the peptide of the invention, i.e. encode no other peptide or polypeptide.

Such a nucleic acid molecule can be synthesised in accordance with methods known in the art. Due to the degeneracy of the genetic code, one of ordinary skill in the art will appreciate that nucleic acid molecules of different nucleotide sequence can encode the same amino acid sequence.

In a fourth aspect, the invention provides a vector comprising a nucleic acid sequence according to the third aspect of the invention. The vector may include, in addition to a nucleic acid sequence encoding only a peptide of the invention, one or more additional nucleic acid sequences encoding one or more additional peptides. Such additional peptides may, once expressed, be fused to the N-terminus or the C-terminus of the peptide of the invention. In one embodiment, the vector includes a nucleic acid sequence encoding a peptide or protein tag such as, for example, a biotinylation site, a FLAG-tag, a MYC-tag, an HA-tag, a GST-tag, a Strep-tag or a poly-histidine tag.

Suitable vectors are known in the art as is vector construction, including the selection of promoters and other regulatory elements, such as enhancer elements. The vector utilised in the context of the present invention desirably comprises sequences appropriate for introduction into cells. For instance, the vector may be an expression vector, a vector in which the coding sequence of the polypeptide is under the control of its own cis-acting regulatory elements, a vector designed to facilitate gene integration or gene replacement in host cells, and the like.

In the context of the present invention, the term "vector" encompasses a DNA molecule, such as a plasmid, bacteriophage, phagemid, virus or other vehicle, which contains one or more heterologous or recombinant nucleotide sequences (e.g., an above-described nucleic acid molecule of the invention, under the control of a functional promoter and, possibly, also an enhancer) and is capable of functioning as a vector in the sense understood by those of ordinary skill in the art. Appropriate phage and viral vectors include, but are not limited to, lambda (λ) bacteriophage, EMBL bacteriophage, simian virus 40, bovine papilloma virus, Epstein-Barr virus, adenovirus, herpes virus, vaccinia virus, Moloney murine leukemia virus, Harvey murine sarcoma virus, murine mammary tumor virus, lentivirus and Rous sarcoma virus.

In a fifth aspect, the invention provides a cell comprising the vector of the fourth aspect of the invention. The cell may be an antigen presenting cell and is preferably a cell of the immune system. In particular, the cell may be a specialised antigen presenting cell such as a dendritic cell or a B cell. The cell may be a mammalian cell.

Peptides and complexes of the invention can be used to identify and/or isolate binding moieties that bind specifically to the peptide and/or the complex of the invention. Such binding moieties may be used as immunotherapeutic reagents and may include antibodies and TCRs.

In a sixth aspect, the invention provides a binding moiety that binds the polypeptide of the invention. Preferably the binding moiety binds the peptide when said peptide is in complex with MHC. In the latter instance, the binding moiety may bind partially to the MHC, provided that it also binds to the peptide. The binding moiety may bind only the peptide, and that binding may be specific. The binding moiety may bind only the peptide MHC complex and that binding may be specific.

When used with reference to binding moieties that bind the complex of the invention, "specific" is generally used herein to refer to the situation in which the binding moiety does not show any significant binding to one or more alternative polypeptide-MHC complexes other than the polypeptide-MHC complex of the invention. TCRs that bind to one or more, and in particular several, antigens presented by cells that are not the intended target of the TCR, pose an increased risk of toxicity when administered in vivo because of potential off target reactivity. Such highly cross-reactive TCRs are not suitable for therapeutic use.

The binding moiety may be a T cell receptor (TCR). TCRs are described using the International Immunogenetics (IMGT) TCR nomenclature, and links to the IMGT public database of TCR sequences. The unique sequences defined by the IMGT nomenclature are widely known and accessible to those working in the TCR field. For example, they can be found in the "T cell Receptor Factsbook", (2001) LeFranc and LeFranc, Academic Press, ISBN 0-12-441352-8; Lefranc, (2011), Cold Spring Harb Protoc 2011(6): 595-603; Lefranc, (2001), Curr Protoc Immunol Appendix 1: Appendix 10; Lefranc, (2003), Leukemia 17(1): 260-266, and on the IMGT website (IMGT.org)

The TCRs of the invention may be in any format known to those in the art. For example, the TCRs may be αβ heterodimers, or αα or ββ homodimers.

Alpha-beta heterodimeric TCRs have an alpha chain and a beta chain. Broadly, each chain comprises variable, joining and constant region, and the beta chain also usually contains a short diversity region between the variable and joining regions, but this diversity region is often considered as part of the joining region. Each variable region comprises three hypervariable CDRs (Complementarity Determining Regions) embedded in a framework sequence; CDR3 is believed to be the main mediator of antigen recognition. There are several types of alpha chain variable (Vα) regions and several types of beta chain variable (Vβ) regions distinguished by their framework, CDR1 and CDR2 sequences, and by a partly defined CDR3 sequence.

The TCRs of the invention may not correspond to TCRs as they exist in nature. For example, they may comprise alpha and beta chain combinations that are not present in a natural repertoire. Alternatively or additionally they may be soluble, and/or the alpha and/or beta chain constant domain may be truncated relative to the native/naturally occurring TRAC/TRBC sequences such that, for example, the C terminal transmembrane domain and intracellular regions are not present. Such truncation may result in removal of the cysteine residues from TRAC/TRBC that form the native interchain disulphide bond.

In addition the TRAC/TRBC domains may contain modifications. For example, the alpha chain extracellular sequence may include a modification relative to the native/naturally occurring TRAC whereby amino acid T48 of TRAC, with reference to IMGT numbering, is replaced with C48. Likewise, the beta chain extracellular sequence may include a modification relative to the native/naturally occurring TRBC1 or TRBC2 whereby S57 of TRBC1 or TRBC2, with reference to IMGT numbering, is replaced with C57. These cysteine substitutions relative to the native alpha and beta chain extracellular sequences enable the formation of a non-native interchain disulphide bond which stabilises the refolded soluble TCR, i.e. the TCR formed by refolding extracellular alpha and beta chains (WO 03/020763). This non-native disulphide bond facilitates the display of correctly folded TCRs on phage. (Li et al., Nat Biotechnol 2005 March; 23(3):349-54). In addition the use of the stable disulphide linked soluble TCR enables more convenient assessment of binding affinity and binding half-life. Alternative positions for the formation of a non-native disulphide bond are described in WO 03/020763. These include Thr 45 of exon 1 of TRAC*01 and Ser 77 of exon 1 of TRBC1*01 or TRBC2*01; Tyr 10 of exon 1 of TRAC*01 and Ser 17 of exon 1 of TRBC1*01 or TRBC2*01; Thr 45 of exon 1 of TRAC*01 and Asp 59 of exon 1 of TRBC1*01 or TRBC2*01; and Ser 15 of exon 1 of TRAC*01 and Glu 15 of exon 1 of TRBC1*01 or TRBC2*01. TCRs with a non-native disulphide bond may be full length or may be truncated.

TCRs of the invention may be in single chain format (such as those described in WO9918129). Single chain TCRs include αβ TCR polypeptides of the type: Vα-L-Vβ, Vβ-L-Vα, Vα-Cα-L-Vβ, Vα-L-Vβ-Cβ or Vα-Cα-L-Vβ-Cβ, optionally in the reverse orientation, wherein Vα and Vβ are TCR α and β variable regions respectively, Cα and Cβ are TCR α and β constant regions respectively, and L is a linker sequence. Single chain TCRs may contain a non-native disulphide bond. The TCR may be in a soluble form (i.e. having no transmembrane or cytoplasmic domains), or may contain full length alpha and beta chains. The TCR may be provided on the surface of a cell, such as a T cell.

TCRs of the invention may be engineered to include mutations. Methods for producing mutated high affinity TCR variants such as phage display and site directed mutagenesis and are known to those in the art (for example see WO 04/044004 and Li et al., Nat Biotechnol 2005 March; 23(3):349-54).). Preferably, mutations to improve affinity are made within the variable regions of alpha and/or beta chains. More preferably mutations to improve affinity are made within the CDRs. There may be between 1 and 15 mutations in the alpha and or beta chain variable regions.

TCRs of the invention may also be may be labelled with an imaging compound, for example a label that is suitable for diagnostic purposes. Such labelled high affinity TCRs are useful in a method for detecting a TCR ligand selected from CD1-antigen complexes, bacterial superantigens, and MHC-peptide/superantigen complexes, which method comprises contacting the TCR ligand with a high affinity TCR (or a multimeric high affinity TCR complex) which is specific for the TCR ligand; and detecting binding to the TCR ligand. In multimeric high affinity TCR complexes such as those described in Zhu et al., J. Immunol. 2006 Mar. 1; 176(5): 3223-32, (formed, for example, using biotinylated heterodimers) fluorescent streptavidin (commercially available) can be used to provide a detectable label. A fluorescently-labelled multimer is suitable for use in FACS analysis, for example to detect antigen presenting cells carrying the peptide for which the high affinity TCR is specific.

A TCR of the present invention (or multivalent complex thereof) may alternatively or additionally be associated with (e.g. covalently or otherwise linked to) a therapeutic agent which may be, for example, a toxic moiety for use in cell killing, or an immunostimulating agent such as an interleukin or a cytokine. A multivalent high affinity TCR complex of the present invention may have enhanced binding capability for a TCR ligand compared to a non-multimeric wild-type or high affinity T cell receptor heterodimer. Thus, the multivalent high affinity TCR complexes according to the invention are particularly useful for tracking or targeting cells presenting particular antigens in vitro or in vivo, and are also useful as intermediates for the production of further multivalent high affinity TCR complexes having such uses. The high affinity TCR or multivalent high affinity TCR complex may therefore be provided in a pharmaceutically acceptable formulation for use in vivo.

High affinity TCRs of the invention may be used in the production of soluble bi-specific reagents. A preferred embodiment is a reagent which comprises a soluble TCR, fused via a linker to an anti-CD3 specific antibody fragment. Further details including how to produce such reagents are described in WO10/133828.

In a further aspect, the invention provides nucleic acid encoding the TCR of the invention, a TCR expression vector comprising nucleic acid encoding a TCR of the invention, as well as a cell harbouring such a vector. The TCR may be encoded either in a single open reading frame or two distinct open reading frames. Also included in the scope of the invention is a cell harbouring a first expression vector which comprises nucleic acid encoding an alpha chain of a TCR of the invention, and a second expression vector which comprises nucleic acid encoding a beta chain of a TCR of the invention. Alternatively, one vector may encode both an alpha and a beta chain of a TCR of the invention.

A further aspect of the invention provides a cell displaying on its surface a TCR of the invention. The cell may be a T cell, or other immune cell. The T cell may be modified such that it does not correspond to a T cell as it exists in nature. For example, the cell may be transfected with a vector encoding a TCR of the invention such that the T cell expresses a further TCR in addition to the native TCR. Additionally or alternatively the T cell may be modified such that it is not able to present the native TCR. There are a number of methods suitable for the transfection of T cells with DNA or RNA encoding the TCRs of the invention (see for example Robbins et al., J. Immunol. 2008 May 1; 180(9):6116-31). T cells expressing the TCRs of the invention are suitable for use in adoptive therapy-based treatment of diseases such as cancers. As will be known to those skilled in the art there are a number of suitable methods by which adoptive therapy can be carried out (see for example Rosenberg et al., Nat Rev Cancer. 2008 April; 8(4):299-308).

The TCRs of the invention intended for use in adoptive therapy are generally glycosylated when expressed by the transfected T cells. As is well known, the glycosylation pattern of transfected TCRs may be modified by mutations of the transfected gene (Kuball J et al., J Exp Med. 2009 Feb. 16; 206(2):463-75).

Examples of TCR variable region amino acid sequences that are able to specifically recognise peptides of the invention are provided in the Figures. TCRs having 90, 91, 92, 93, 94, 95, 96, 97, 98 or 99% identity to the sequences provided are also contemplated by the invention. TCRs with the same alpha and beta chain usage are also included in the invention.

The binding moiety of the invention may be an antibody. The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term "antibody" includes antibody fragments, derivatives, functional equivalents and homologues of antibodies, humanised antibodies, including any polypeptide comprising an immunoglobulin binding domain, whether natural or wholly or partially synthetic and any polypeptide or protein having a binding domain which is, or is homologous to, an antibody binding domain. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to herein as "mab".

It is possible to take an antibody, for example a monoclonal antibody, and use recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin (see, for instance, EP-A-184187, GB 2188638A or EP-A-239400). A hybridoma (or other cell that produces antibodies) may be subject to genetic mutation or other changes, which may or may not alter the binding specificity of antibodies produced.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature. 1989 Oct. 12; 341 (6242):544-6) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science. 1988 Oct. 21; 242(4877):423-6; Huston et al., Proc Natl Acad Sci USA. 1988 August; 85(16):5879-83; (viii) bispecific single chain Fv dimers (PCT/US92/09965) and (ix) "diabodies", multivalent or multispecific fragments constructed by gene fusion (WO94/13804; P. Hollinger et al., Proc Natl Acad Sci USA. 1993 Jul. 15; 90(14):6444-8). Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). Where bispecific antibodies are to be used, these may be conventional bispecific antibodies, which can be manufactured in a variety of ways (Hollinger & Winter, Curr Opin Biotechnol. 1993 August; 4(4):446-9), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO J. 1991 December; 10(12):3655-9). Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

The binding moiety may be an antibody-like molecule that has been designed to specifically bind a peptide-MHC complex of the invention. Of particular preference are TCR-mimic antibodies, such as, for example those described in WO2007143104 and Sergeeva et al., Blood. 2011 Apr. 21; 117(16):4262-72 and/or Dahan and Reiter. Expert Rev Mol Med. 2012 Feb. 24; 14:e6.

Also encompassed within the present invention are binding moieties based on engineered protein scaffolds. Protein scaffolds are derived from stable, soluble, natural protein structures which have been modified to provide a binding site for a target molecule of interest. Examples of engineered protein scaffolds include, but are not limited to, affibodies, which are based on the Z-domain of staphylococcal protein A that provides a binding interface on two of its a-helices (Nygren, FEBS J. 2008 June; 275(11):2668-76); anticalins, derived from lipocalins, that incorporate binding sites for small ligands at the open end of a beta-barrel fold (Skerra, FEBS J. 2008 June; 275(11):2677-83), nanobodies, and DARPins. Engineered protein scaffolds are typically targeted to bind the same antigenic proteins as antibodies, and are potential therapeutic agents. They may act as inhibitors or antagonists, or as delivery vehicles to target molecules, such as toxins, to a specific tissue in vivo (Gebauer and Skerra, Curr Opin Chem Biol. 2009 June; 13(3):245-55). Short peptides may also be used to bind a target protein. Phylomers are natural structured peptides derived from bacterial genomes. Such peptides represent a diverse array of protein structural folds and can be used to inhibit/disrupt protein-protein interactions in vivo (Watt, Nat Biotechnol. 2006 February; 24(2):177-83)].

In another aspect, the invention further provides a peptide of the invention, a nucleic acid molecule of the invention, a vector of the invention, a cell of the invention or a binding moiety of the invention for use in medicine. The peptide, complex, nucleic acid, vector, cell or binding moiety may be used for in the treatment or prevention of cancer, in particular, breast, colon and oesophageal cancers In a further aspect, the invention provides a pharmaceutical composition comprising a peptide of the invention, a nucleic acid molecule of the invention, a vector of the invention, a cell of the invention or a binding moiety of the invention together with a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms. Suitable compositions and methods of administration are known to those skilled in the art, for example see, Johnson et al., Blood. 2009 Jul. 16; 114(3):535-46, with reference to clinical trial numbers NCI-07-C-0175 and NCI-07-C-0174. Cells in accordance with the invention will usually be supplied as part of a sterile, pharmaceutical composition which will normally include a pharmaceutically acceptable carrier. For example, T cells transfected with TCRs of the invention may be provided in pharmaceutical composition together with a pharmaceutically acceptable carrier. The pharmaceutically acceptable carrier may be a cream, emulsion, gel, liposome, nanoparticle or ointment.

The pharmaceutical composition may be adapted for administration by any appropriate route such as a parenteral (including subcutaneous, intramuscular, or intravenous), enteral (including oral or rectal), inhalation or intranasal routes. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated (such as cancer, viral infection or autoimmune disease), the age and condition of the individual to be treated, etc. For example, a suitable dose range for a reagent comprising a soluble TCR fused to an anti-CD3 domain may be between 25 ng/kg and 50 µg/kg. A physician will ultimately determine appropriate dosages to be used.

The polypeptide of the invention may be provided in the form of a vaccine composition. The vaccine composition may be useful for the treatment or prevention of cancer. All such compositions are encompassed in the present invention. As will be appreciated, vaccines may take several forms (Schlom, J Natl Cancer Inst. 2012 Apr. 18; 104(8): 599-613). For example, the peptide of the invention may be used directly to immunise patients (Salgaller, Cancer Res. 1996 Oct. 15; 56(20):4749-57 and Marchand, Int J Cancer. 1999 Jan. 18; 80(2):219-30). The vaccine composition may include additional peptides such that the peptide of the invention is one of a mixture of peptides. Adjuvants may be added to the vaccine composition to augment the immune response Alternatively the vaccine composition may take the form of an antigen presenting cell displaying the peptide of the invention in complex with MHC. Preferably the antigen presenting cell is an immune cell, more preferably a dendritic cell. The peptide may be pulsed onto the surface of the cell (Thurner, J Exp Med. 1999 Dec. 6; 190(11):1669-78), or nucleic acid encoding for the peptide of the invention may be introduced into dendritic cells (for example by electroporation. Van Tendeloo, Blood. 2001 Jul. 1; 98(1):49-56).

The polypeptides, complexes, nucleic acid molecules, vectors, cells and binding moieties of the invention may be non-naturally occurring and/or purified and/or engineered and/or recombinant and/or isolated and/or synthetic.

The invention also provides a method of identifying a binding moiety that binds a complex of the invention, the method comprising contacting a candidate binding moiety with the complex and determining whether the candidate binding moiety binds the complex. Methods to determine binding to polypeptide-MHC complexes are well known in the art. Preferred methods include, but are not limited to, surface plasmon resonance, or any other biosensor technique, ELISA, flow cytometry, chromatography, microscopy. Alternatively, or in addition, binding may be determined by functional assays in which a biological response is detected upon binding, for example, cytokine release or cell apoptosis.

The candidate binding moiety may be a binding moiety of the type already described, such as a TCR or an antibody. Said binding moiety may be obtained using methods that are known in the art.

For example, antigen binding T cells and TCRs have traditionally been isolated from fresh blood obtained from patients or healthy donors. Such a method involves stimulating T cells using autologous DCs, followed by autologous B cells, pulsed with the polypeptide of the invention. Several rounds of stimulation may be carried out, for example three or four rounds. Activated T cells may then be tested for specificity by measuring cytokine release in the presence of T2 cells pulsed with the peptide of the invention (for example using an IFNγ ELISpot assay). Activated cells may then be sorted by fluorescence-activated cell sorting (FACS) using labelled antibodies to detect intracellular cytokine production (e.g. IFNγ), or expression of a cell surface marker (such as CD137). Sorted cells may be expanded and further validated, for example, by ELISpot assay and/or cytotoxicity against target cells and/or staining by peptide-MHC tetramer. The TCR chains from validated clones may then be amplified by rapid amplification of cDNA ends (RACE) and sequenced.

Alternatively, TCRs and antibodies may be obtained from display libraries in which the peptide MHC complex of the invention is used to pan the library The production of antibody libraries using phage display is well known in the art, for example see Aitken, Antibody phage display: Methods and Protocols (2009, Humana, New York). TCRs can be displayed on the surface of phage particles and yeast particles for example, and such libraries have been used for the isolation of high affinity variants of TCR derived from T cell clones (as described in WO04044004 and Li et al. *Nat Biotechnol.* 2005 March; 23(3):349-54 and WO9936569). It has been demonstrated more recently that TCR phage libraries can be used to isolate TCRs with novel antigen specificity. Such libraries are typically constructed with alpha and beta chain sequences corresponding to those found in a natural repertoire. However, the random combination of these alpha and beta chain sequences, which occurs during library creation, produces a repertoire of TCRs not present in nature (as described in WO2015/136072, PCT/EP2016/071757, PCT/EP2016/071761, PCT/EP2016/071762, PCT/EP2016/071765, PCT/EP2016/071767, PCT/EP2016/071768, PCT/EP2016/071771 and PCT/EP2016/071772)

In a preferred embodiment, the peptide-MHC complex of the invention may be used to screen a library of diverse TCRs displayed on the surface of phage particles. The TCRs displayed by said library may not correspond to those contained in a natural repertoire, for example, they may contain alpha and beta chain pairing that would not be present in vivo, and or the TCRs maycontain non-natural mutations and or the TCRs may be in soluble form. Screening may involve panning the phage library with peptide-MHC complexes of the invention and subsequently isolating bound phage. For this purpose peptide-MHC complexes may be attached to a solid support, such as a magnet bead, or column matrix and phage bound peptide MHC complexes isolated, with a magnet, or by chromatography, respectively. The panning steps may be repeated several times for example three or four times. Isolated phage may be further expanded in E. coli cells. Isolated phage particles may be tested for specific binding peptide-MHC complexes of the invention. Binding can be detected using techniques including, but not limited to, ELISA, or SPR for example using a BiaCore instrument. The DNA sequence of the T cell receptor displayed by peptide-MHC binding phage can be further identified by standard PCR methods.

Preferred or optional features of each aspect of the invention are as for each of the other aspects mutatis mutandis. The prior art documents mentioned herein are incorporated by reference to the fullest extent permitted by law.

The present invention will be further illustrated in the following Examples and Figures which are given for illustration purposes only and are not intended to limit the invention in any way.

BRIEF DESCRIPTION OF THE FIGURES

FIG. 5 shows the amino acid sequences of the respective alpha chain and beta chain variable chains of the TCRs of FIG. 4.

EXAMPLES

Example 1

Identification of Target-derived Peptides by Mass Spectrometry

Presentation of HLA-restricted peptides derived from LGSN on the surface of tumour cell lines was investigated using mass spectrometry.

Method

Immortalised cell lines obtained from commercial sources were maintained and expanded under standard conditions.

Class I HLA complexes were purified by immunoaffinity using commercially available anti-HLA antibodies BB7.1 (anti-HLA-B*07), BB7.2 (anti-HLA-A*02) and W6/32 (anti-Class 1). Briefly, cells were lysed in buffer containing non-ionic detergent NP-40 (0.5% v/v) at $5 \times 10^7$ cells per ml and incubated at 4° C. for 1 h with agitation/mixing. Cell debris was removed by centrifugation and supernatant precleared using proteinA-Sepharose. Supernatant was passed over 5 ml of resin containing 8 mg of anti-HLA antibody immobilised on a proteinA-Sepharose scaffold. Columns were washed with low salt and high salt buffers and complexes eluted in acid. Eluted peptides were separated from HLA complexes by reversed phase chromatography using a solid phase extraction cartridge (Phenomenex). Bound material was eluted from the column and reduced in volume using a vacuum centrifuge.

Peptides were separated by high pressure liquid chromatography (HPLC) on a Dionex Ultimate 3000 system using a C18 column (Phenomenex). Peptides were loaded in 98% buffer A (0.1% aqueous trifluoroacetic acid (TFA)) and 2% buffer B (0.1% TFA in acetonitrile). Peptides were eluted using a stepped gradient of B (2-60%) over 20 min. Fractions were collected at one minute intervals and lyophilised.

Peptides were analysed by nanoLCMS/MS using a Dionex Ultimate 3000 nanoLC coupled to either AB Sciex Triple TOF 5600 or Thermo Orbitrap Fusion mass spectrometers. Both machines were equipped with nanoelectrospray ion sources. Peptides were loaded onto an Acclaim PepMap 100 trap column (Dionex) and separated using an Acclaim PepMap RSLC column (Dionex). Peptides were loaded in mobile phase A (0.5% formic acid:water) and eluted using a gradient of buffer B (acetonitrile:0.5% formic acid) directly into the nanospray ionisation source.

For peptide identification the mass spectrometer was operated using an information dependent acquisition (IDA) workflow. Information acquired in these experiments was used to search the Uniprot database of human proteins for peptides consistent with the fragmentation patterns seen, using Protein pilot software (Ab Sciex) and PEAKS software (Bioinformatics solutions). Peptides identified are assigned a score by the software, based on the match between the observed and expected fragmentation patterns.

Results

The polypeptides set out in table 1, corresponding to SEQ ID NOs: 1-3, were detected by mass spec following extraction from cancer cell lines. An example cell line from which the peptide was detected is indicated in the table along with the HLA antibody used for immunoaffinity purification.

| SEQ ID NO | Amino acid sequence | HLA antibody | Example cancer cell line |
| --- | --- | --- | --- |
| 1 | ALGETFIRYFV | HLA-A*02 | NCI H2023 |
| 2 | LSCLMAPSV | class I | BM1604 |
| 3 | QILTPPQL | class I | NCI H1944 |

Figure 1:
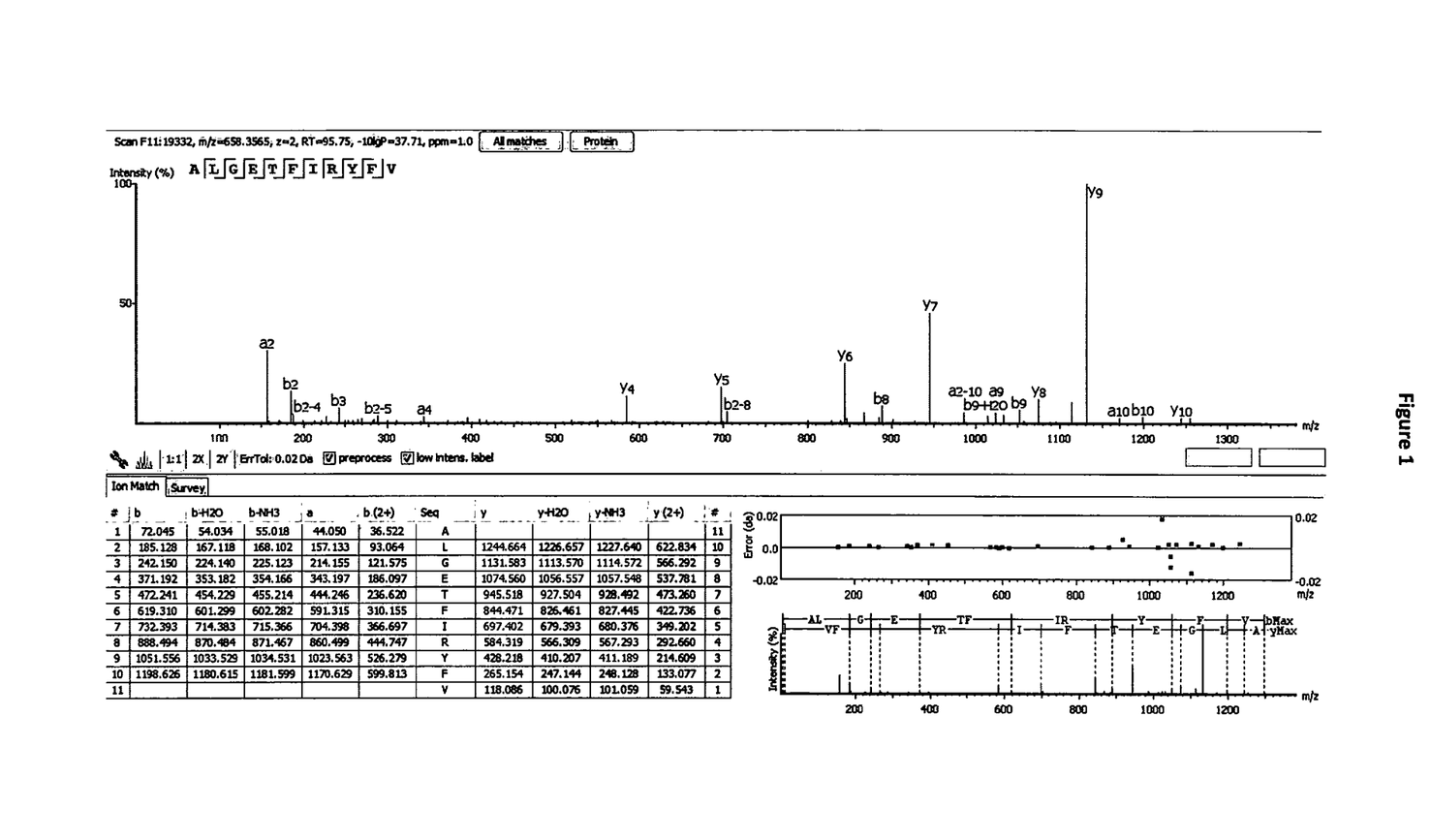
FIGS. 1 to 3 show the respective fragmentation spectra for the peptides of SEQ ID NOS: 1 to 3, eluted from cells. A table highlighting the matching ions is shown below each spectrum.
Figure 2:
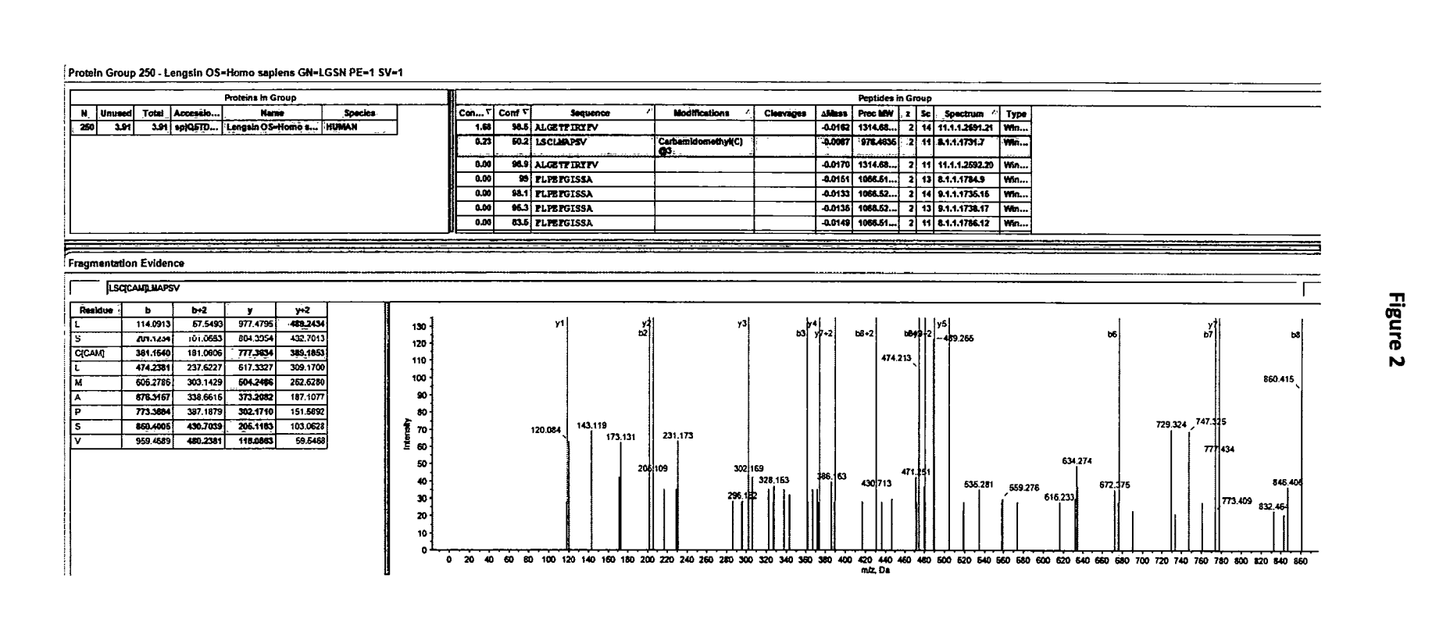
Figure 3:
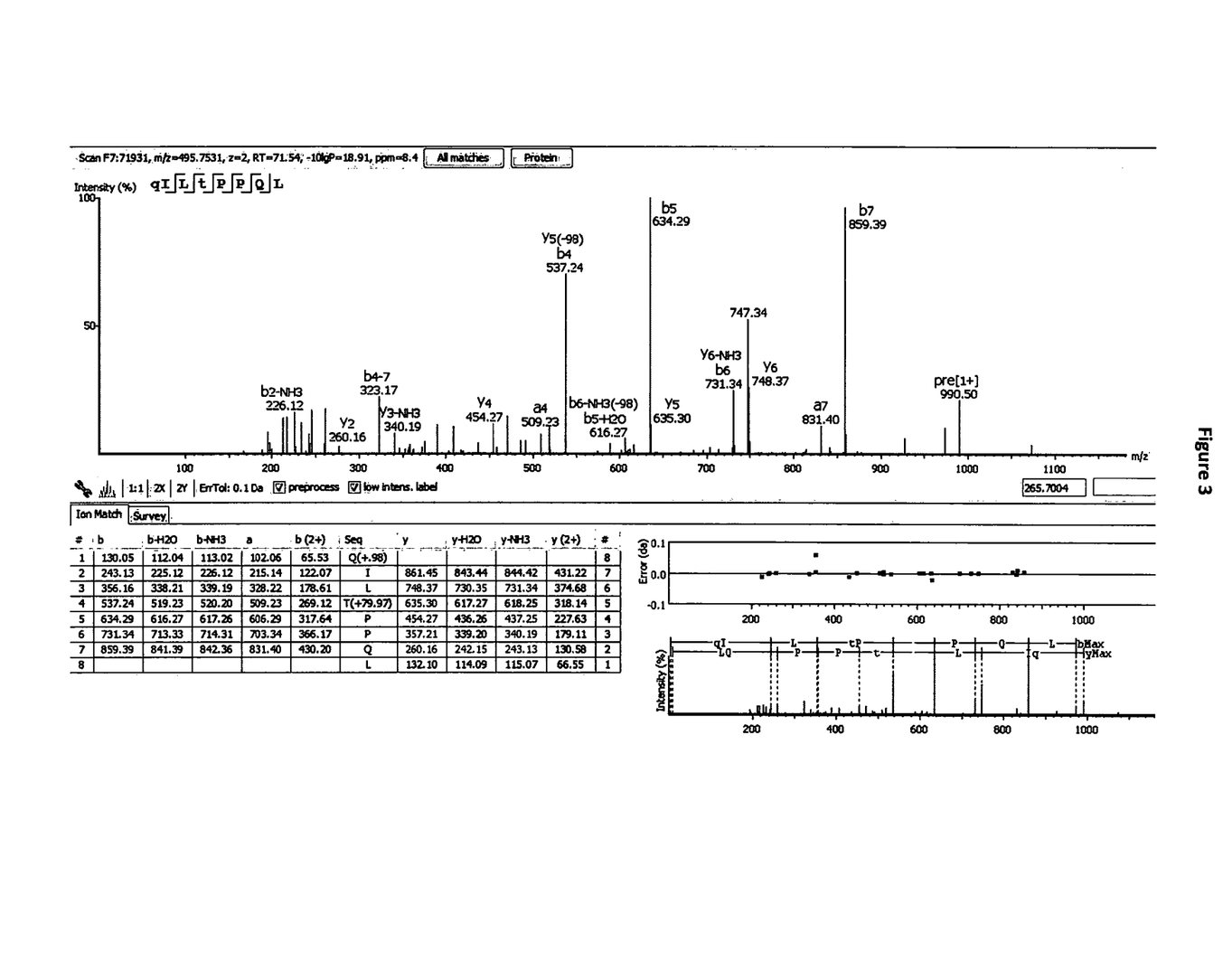

FIGS. 1-3 show representative fragmentation patterns for the peptides of SEQ ID NOS: 1-3 respectively. A table highlighting the matching ions is shown below each spectrum.

Example 2

Preparation of Recombinant Peptide-HLA Complexes

The following describes a suitable method for the preparation of soluble recombinant HLA loaded with TAA peptide.

Class I HLA molecules (HLA-heavy chain and HLA light-chain (β2m)) were expressed separately in E. coli as inclusion bodies, using appropriate constructs. HLA-heavy chain additionally contained a C-terminal biotinylation tag which replaces the transmembrane and cytoplasmic domains (O'Callaghan et al. (1999) Anal. Biochem. 266: 9-15). E. coli cells were lysed and inclusion bodies processed to approximately 80% purity.

Inclusion bodies of β2m and heavy chain were denatured separately in denaturation buffer (6 M guanidine, 50 mM Tris pH 8.1, 100 mM NaCl, 10 mM DTT, 10 mM EDTA) for 30 mins at 37° C. Refolding buffer was prepared containing 0.4 M L-Arginine, 100 mM Tris pH 8.1, 2 mM EDTA, 3.1 mM cystamine dihydrochloride, 7.2 mM cysteamine hydrochloride. Synthetic peptide was dissolved in DMSO to a final concentration of 4 mg/ml and added to the refold buffer at 4 mg/litre (final concentration). Then 30 mg/litre β2m followed by 60 mg/litre heavy chain (final concentrations) are added. Refolding was allowed to reach completion at room temperature for at least 1 hour.

The refold mixture was then dialysed against 20 L of deionised water at 4° C. for 16 h, followed by 10 mM Tris pH 8.1 for a further 16 h. The protein solution was then filtered through a 0.45 µm cellulose acetate filter and loaded onto a POROS HQ anion exchange column (8 ml bed volume) equilibrated with 20 mM Tris pH 8.1. Protein was eluted with a linear 0-500 mM NaCl gradient using an AKTA purifier (GE Healthcare). HLA-peptide complex eluted at approximately 250 mM NaCl, and peak fractions were collected, a cocktail of protease inhibitors (Calbiochem) was added and the fractions were chilled on ice.

Biotinylation tagged pHLA molecules were buffer exchanged into 10 mM Tris pH 8.1, 5 mM NaCl using a GE Healthcare fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 µg/ml BirA enzyme (purified according to O'Callaghan et al., (1999) Anal. Biochem. 266: 9-15). The mixture was then allowed to incubate at room temperature overnight.

The biotinylated pHLA molecules were further purified by gel filtration chromatography using an AKTA purifier with a GE Healthcare Superdex 75 HR 10/30 column pre-equilibrated with filtered PBS. The biotinylated pHLA mixture was concentrated to a final volume of 1 ml loaded onto the column and was developed with PBS at 0.5 ml/min. Biotinylated pHLA molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA molecules were stored frozen at −20° C.

Such peptide-MHC complexes may be used in soluble form or may be immobilised through their C terminal biotin moiety on to a solid support, to be used for the detection of T cells and T cell receptors which bind said complex. For example, such complexes can be used in panning phage libraries, performing ELISA assays and preparing sensor chips for BIACORE measurements.

Example 3

Identification of TCRs that Bind to a Peptide-MHC Complex of the Invention

Method

Antigen binding TCRs were obtained using peptides of the invention to pan a TCR phage library. The library was constructed using alpha and beta chain sequences obtained from a natural repertoire (as described in WO2015/136072, PCT/EP2016/071757, PCT/EP2016/071761, PCT/EP2016/071762, PCT/EP2016/071765, PCT/EP2016/071767, PCT/EP2016/071768, PCT/EP2016/071771 or PCT/EP2016/071772). The random combination of these alpha and beta chain sequences, which occurs during library creation, produces a non-natural repertoire of alpha beta chain combinations.

TCRs obtained from the library were assessed by ELISA to confirm specific antigen recognition. ELISA assays were performed as described in WO2015/136072. Briefly, 96 well MaxiSorp ELISA plates were coated with streptavidin and incubated with the biotinylated peptide-HLA complex of the invention. TCR bearing phage clones were added to each well and detection carried out using an anti-M13-HRP antibody conjugate. Bound antibody was detected using the KPL labs TMB Microwell peroxidase Substrate System. The appearance of a blue colour in the well indicated binding of the TCR to the antigen. An absence of binding to alternative peptide-HLA complexes indicated the TCR is not highly cross reactive.

Further confirmation that TCRs are able to bind a complex of comprising a peptide HLA complex of the invention can be obtained by surface plasmon resonance (SPR) using isolated TCRs. In this case alpha and beta chain sequences are expressed in *E. coli* as soluble TCRs, (WO2003020763; Boulter, et al., Protein Eng, 2003. 16: 707-711). Binding of the soluble TCRs to the complexes is analysed by surface plasmon resonance using a BIACORE 3000 instrument. Biotinylated peptide-HLA monomers are prepared as previously described (Example 2) and immobilized on to a streptavidin-coupled CM-5 sensor chip. All measurements are performed at 25° C. in PBS buffer supplemented with 0.005% Tween at a constant flow rate. To measure affinity, serial dilutions of the soluble TCRs are flowed over the immobilized peptide-MHCs and the response values at equilibrium determined for each concentration. Data are analysed by plotting the specific equilibrium binding against protein concentration followed by a least squares fit to the Langmuir binding equation, assuming a 1:1 interaction.

Results

Figure 4:
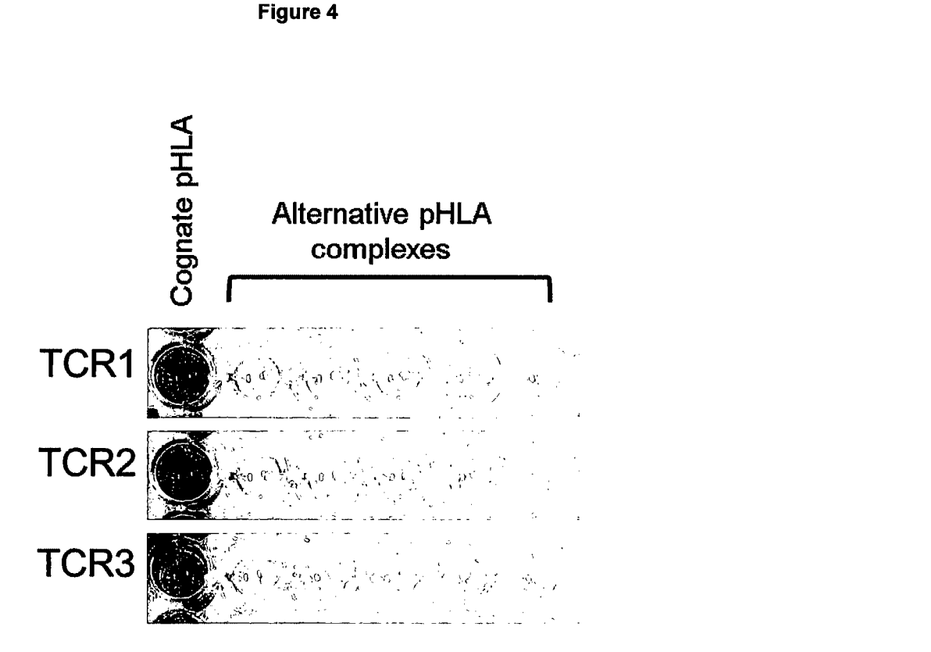
FIG. 4 shows ELISA plates demonstrating the specificity of TCRs for a complex of the peptide of SEQ ID NO: 1 and HLA-A*02, by comparing binding with other peptide-HLA-A*02 complexes.

TCRs that specifically recognise peptide-HLA complexes of the invention were obtained from the library. FIG. 4 shows ELISA data for three such TCRs.

Amino acid sequences of the TCR alpha and beta variable regions of the TCRs identified in FIG. 4 are provided in FIG. 5.

These data confirm that antigen specific TCRs can be isolated.

The invention claimed is:

1. A method of effecting an in vivo immune response to cells expressing Lengsin (LGSN), in a subject with non-small cell lung cancer, comprising:
administering to the subject a therapeutically effective amount of a soluble T cell receptor ("TCR") fused to an anti-CD3 specific antibody fragment,
wherein the TCR is capable of specifically binding a polypeptide complexed with HLA-A*02,
wherein the polypeptide is 8 to 16 amino acids in length and comprises
the amino acid sequence of SEQ ID NO: 1.

2. The method of claim 1, wherein the polypeptide is 11 amino acids in length.

3. The method of claim 2, wherein the polypeptide has the amino acid sequence of SEQ ID NO: 1.

4. The method of claim 3, wherein the TCR is a heterodimeric TCR comprising an alpha chain, the alpha chain comprising a Vα variable region, and a beta chain comprising a Vβ variable region.

5. The method of claim 4, wherein the alpha chain variable region and the beta chain variable region of the heterodimeric TCR comprises the CDRs of the variable regions respectively selected from SEQ ID NO: 4 and SEQ ID NO: 5, SEQ ID NO: 6 and SEQ ID NO: 7, and SEQ ID NO: 8 and SEQ ID NO: 9.

6. A method of adoptive cell therapy in a subject with non-small cell lung cancer,
comprising:
administering to the subject T cells transfected with a vector encoding a TCR capable of specifically binding a polypeptide complexed with HLA-A *02,
wherein the polypeptide is 8 to 16 amino acids in length and comprises the amino acid sequence of SEQ ID NO: 1.

7. The method of claim 6, wherein the polypeptide is 11 amino acids in length.

8. The method of claim 7, wherein the polypeptide has the amino acid sequence of SEQ ID NO: 1.

9. The method of claim 8, wherein the TCR is a heterodimeric TCR comprising an alpha chain, the alpha chain comprising a Vα variable region, and a beta chain comprising a Vβ variable region.

10. The method of claim 9, wherein the alpha chain variable region and the beta chain variable region of the heterodimeric TCR comprises the CDRs of the variable regions respectively selected from SEQ ID NO: 4 and SEQ ID NO: 5, SEQ ID NO: 6 and SEQ ID NO: 7, and SEQ ID NO: 8 and SEQ ID NO: 9.

* * * * *

UNITED STATES PATENT AND TRADEMARK OFFICE
CERTIFICATE OF CORRECTION

PATENT NO. : 10,851,366 B2
APPLICATION NO. : 15/777621
DATED : December 1, 2020
INVENTOR(S) : Alex Powlesland et al.

It is certified that error appears in the above-identified patent and that said Letters Patent is hereby corrected as shown below:

On the Title Page

Item (51), in Column 1, under "Int. Cl.", Line 2, after "C12N" delete "9/00" and insert -- 9/93 --

Signed and Sealed this
Twenty-third Day of August, 2022

Katherine Kelly Vidal
*Director of the United States Patent and Trademark Office*

SEQUENCE LISTING

```
<160> NUMBER OF SEQ ID NOS: 9

<210> SEQ ID NO 1
<211> LENGTH: 11
<212> TYPE: PRT
<213> ORGANISM: Homo sapiens

<400> SEQUENCE: 1

Ala Leu Gly Glu Thr Phe Ile Arg Tyr Phe Val
1               5                   10

<210> SEQ ID NO 2
<211> LENGTH: 9
<212> TYPE: PRT
```

```
<213> ORGANISM: Homo sapiens

<400> SEQUENCE: 2

Leu Ser Cys Leu Met Ala Pro Ser Val
1               5

<210> SEQ ID NO 3
<211> LENGTH: 8
<212> TYPE: PRT
<213> ORGANISM: Homo sapiens

<400> SEQUENCE: 3

Gln Ile Leu Thr Pro Pro Gln Leu
1               5

<210> SEQ ID NO 4
<211> LENGTH: 111
<212> TYPE: PRT
<213> ORGANISM: Homo sapiens

<400> SEQUENCE: 4

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Met Asp Ser Ser
                85                  90                  95

Tyr Lys Leu Ile Phe Gly Ser Gly Thr Arg Leu Leu Val Arg Pro
            100                 105                 110

<210> SEQ ID NO 5
<211> LENGTH: 109
<212> TYPE: PRT
<213> ORGANISM: Homo sapiens

<400> SEQUENCE: 5

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Asn Ser Met
                20                  25                  30

Tyr Trp Tyr Arg Gln Asp Pro Gly Met Gly Leu Arg Leu Ile Tyr Tyr
            35                  40                  45

Ser Ala Ser Glu Gly Thr Thr Asp Lys Gly Glu Val Pro Asn Gly Tyr
        50                  55                  60

Asn Val Ser Arg Leu Asn Lys Arg Glu Phe Ser Leu Arg Leu Glu Ser
65                  70                  75                  80

Ala Ala Pro Ser Gln Thr Ser Val Tyr Phe Cys Ala Ser Gly Phe Tyr
                85                  90                  95

Gly Tyr Thr Phe Gly Ser Gly Thr Arg Leu Thr Val Val
            100                 105

<210> SEQ ID NO 6
<211> LENGTH: 110
```

```
<212> TYPE: PRT
<213> ORGANISM: Homo sapiens

<400> SEQUENCE: 6

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Gly Tyr Gln
                85                  90                  95

Lys Val Thr Phe Gly Thr Gly Thr Lys Leu Gln Val Ile Pro
                100                 105                 110

<210> SEQ ID NO 7
<211> LENGTH: 111
<212> TYPE: PRT
<213> ORGANISM: Homo sapiens

<400> SEQUENCE: 7

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ser Trp Tyr Arg Gln Asp Pro Gly Met Gly Leu Arg Leu Ile His Tyr
            35                  40                  45

Ser Val Gly Ala Gly Ile Thr Asp Gln Gly Glu Val Pro Asn Gly Tyr
50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Pro Gly
                85                  90                  95

Ile Gly Glu Leu Phe Phe Gly Gly Ser Arg Leu Thr Val Leu
                100                 105                 110

<210> SEQ ID NO 8
<211> LENGTH: 113
<212> TYPE: PRT
<213> ORGANISM: Homo sapiens

<400> SEQUENCE: 8

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Ala Gln Gly
```

```
                        85                  90                  95
Gly Ser Glu Lys Leu Val Phe Gly Lys Gly Thr Lys Leu Thr Val Asn
            100                 105                 110
Pro

<210> SEQ ID NO 9
<211> LENGTH: 116
<212> TYPE: PRT
<213> ORGANISM: Homo sapiens

<400> SEQUENCE: 9

Asn Ala Gly Val Thr Gln Thr Pro Lys Phe Arg Ile Leu Lys Ile Gly
1               5                   10                  15

Gln Ser Met Thr Leu Gln Cys Thr Gln Asp Met Asn His Asn Tyr Met
            20                  25                  30

Tyr Trp Tyr Arg Gln Asp Pro Gly Met Gly Leu Lys Leu Ile Tyr Tyr
        35                  40                  45

Ser Val Gly Ala Gly Ile Thr Asp Lys Gly Glu Val Pro Asn Gly Tyr
    50                  55                  60

Asn Val Ser Arg Ser Thr Thr Glu Asp Phe Pro Leu Arg Leu Glu Leu
65                  70                  75                  80

Ala Ala Pro Ser Gln Thr Ser Val Tyr Phe Cys Ala Ser Ser Tyr Leu
                85                  90                  95

Gly Gln Asp Pro Glu Gly Ala Glu Ala Phe Phe Gly Gln Gly Thr Arg
            100                 105                 110

Leu Thr Val Val
        115
```